United States Patent
Shaw et al.

(10) Patent No.: US 10,543,133 B2
(45) Date of Patent: Jan. 28, 2020

(54) COMPONENT FOR A WOUND DRESSING

(75) Inventors: Helen Louise Shaw, Deeside (GB);
David Colin Pritchard, Deeside (GB);
Bryony Jayne Lee, Deeside (GB);
Stephen Mark Bishop, Deeside (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 555 days.

(21) Appl. No.: 13/509,161

(22) PCT Filed: Nov. 10, 2010

(86) PCT No.: PCT/GB2010/002071
§ 371 (c)(1),
(2), (4) Date: Feb. 25, 2013

(87) PCT Pub. No.: WO2011/058311
PCT Pub. Date: May 19, 2011

(65) Prior Publication Data
US 2013/0197460 A1   Aug. 1, 2013

(30) Foreign Application Priority Data
Nov. 10, 2009   (GB) .................................. 0919659.3

(51) Int. Cl.
*A61F 13/539* (2006.01)

(52) U.S. Cl.
CPC .................................. *A61F 13/539* (2013.01)

(58) Field of Classification Search
CPC .... A61F 13/02; A61F 13/0203; A61F 13/023;
A61F 2013/00748; A61F 2013/0054;
A61F 13/022; A61F 2013/00604; A61F
2013/00744; A61F 2013/00463; A61F
2013/0074; A61F 13/00038; A61F
2013/00523; A61F 13/00029; A61F
2013/00634; A61F 2013/00676; A61F
13/2057; A61F 2013/00638; A61F
2013/00753; A61F 2013/00778; A61F
2013/00931; A61F 2013/00927; A61F
13/0206; A61F 2013/00784; A61F
2013/006; A61L 15/44; A61L 31/16;
(Continued)

(56) References Cited

U.S. PATENT DOCUMENTS 3,622,435 A * 11/1971 Cacella .......................... 442/374
4,538,603 A *  9/1985 Pawelchak et al. ............ 602/56
(Continued)

FOREIGN PATENT DOCUMENTS

EP      433354      6/1991
EP      476576      3/1992
(Continued)

OTHER PUBLICATIONS

JPH11509462, Japanese Publication (Aug. 24, 1999) with English Description.
(Continued)

*Primary Examiner* — Ophelia A Hawthorne
(74) *Attorney, Agent, or Firm* — Taft Stettinius & Hollister LLP

(57) ABSTRACT

An absorbent component for a wound dressing, the component comprising a wound contacting layer comprising gel forming fibres bound to a foam layer.

15 Claims, 3 Drawing Sheets

(58) Field of Classification Search
CPC .... A61L 15/28; A61L 15/42; A61L 2300/608; A61L 2400/04; A61L 24/001; A61L 27/3633; A61L 27/52; A61L 15/64; A61L 26/009
USPC .......... 602/41–46, 52, 56, 58; 424/443, 445, 424/448; 604/304–308, 367; 128/888–889
See application file for complete search history.

(56) References Cited

U.S. PATENT DOCUMENTS

| | | | |
|---|---|---|---|
| 4,977,892 A * | 12/1990 | Ewall | A61F 13/023 523/105 |
| 5,674,524 A | 10/1997 | Scherr et al. | |
| 5,681,579 A * | 10/1997 | Freeman | 424/448 |
| 6,168,800 B1 * | 1/2001 | Dobos et al. | 424/405 |
| 2005/0182347 A1 * | 8/2005 | Bishop | A61F 13/022 602/43 |
| 2010/0292626 A1 * | 11/2010 | Gundersen | A61F 13/063 602/56 |

FOREIGN PATENT DOCUMENTS

| | | | |
|---|---|---|---|
| EP | 0892863 | 1/1999 | |
| GB | 2428581 | 2/2007 | |
| GB | 2464970 A * | 5/2010 | ......... A61F 13/0203 |
| GB | 2464970 A | 5/2010 | |
| JP | 2004-522479 | 12/2001 | |
| JP | 2007-521903 | 2/2002 | |
| WO | 87/05206 | 9/1987 | |
| WO | 90/01954 | 3/1990 | |
| WO | 94/17227 | 8/1994 | |
| WO | 93/12275 | 6/1996 | |
| WO | 97/039170 | 10/1997 | |
| WO | 2002/045761 | 6/2002 | |
| WO | 2004/084961 | 7/2004 | |

OTHER PUBLICATIONS

JP 2005-537903, Amendment,(dated Nov. 12, 2002) With English Translation.
Wound Management and Dressing Selection(2006) Wound Essentials. vol. 1 p.(178-183).
Thomas, Mepliex Border Dressings, (May 21, 2009) http://www.dressings.org/Dressings/mepilex-border.html.
European Patent Office, Third Party Observations in relation to EP20100781979, dated Mar. 5, 2013.
European Patent Office, Third Party Observations in relation to EP Application No. 10781979.9, dated Apr. 7, 2013.
Japanese Office Action Summary, Received Dec. 3, 2014.
Canadian Patent Application No. 2,780,238 Official Action dated Oct. 12, 2016.

* cited by examiner

COMPONENT FOR A WOUND DRESSING

CROSS-REFERENCE

This application is a U.S. National Phase of PCT/GB10/002071, filed Nov. 10, 2010, which claims the benefit of United Kingdom Application No. GB 0919659.3, filed Nov. 10, 2009, which application is incorporated herein by reference.

SUMMARY OF THE INVENTION

The present invention relates to a component for a wound dressing and in particular an absorbent component for a wound dressing, the component for use in direct contact with the wound. The present invention also relates to a wound dressing comprising the component as an absorbent component.

BACKGROUND OF THE INVENTION

It is known to make wound dressings for use on exuding wounds. Such dressings manage the exudate produced by the wound in a variety of ways. For instance, some dressings, mainly those based on foam, manage exudate by absorbing the exudate and allowing the moisture taken up by the dressing to evaporate through the backing or top of the dressing. Such dressings are not designed to absorb and retain the exudate but to absorb and expel the exudate by moisture vapour transmission so that they maximise the level of exudate handled within the limitations of their design. A disadvantage of such dressings is that the lateral spread of the exudate across the dressing is not contained because of the nature of the open structure of the foam and this can cause normal skin surrounding the wound to become macerated as the whole of the dressing surface becomes saturated.

A further disadvantage of the open structure of the foam is that when the dressing is put under pressure, for example when compression is applied or when force is applied to the dressing due to the patient sitting, lying or rolling over, the exudate can be squeezed out of the porous, open foam structure and into contact with the wound and/or surrounding skin surfaces creating the potential for peri-wound maceration and, in the case of chronic wounds, further wound breakdown due to damage caused by certain components of chronic wound exudate.

A further disadvantage of such dressings is that rapid loss of exudate by evaporation can cause the wound surface to become desiccated over time which impedes healing.

Other dressings, mainly those based on absorbents that gel, manage exudate by absorbing it and retaining it within the dressing. The moisture in the absorbent can still be lost by vapour transmission from the dressing, but less readily than with a foam absorbent because the exudate is retained and held within the gelled absorbent. As the absorbent is acting as a reservoir for exudate, it needs to have sufficient capacity to retain exudate throughout the wear time of the dressing. This affects the quantity of absorbent needed in the wound dressing which of course affects the thickness and conformability of the dressing overall. In addition, in general with gelling absorbents, particularly fibrous gelling absorbents, the relationship between the thickness of the gelling absorbent layer or its weight per unit area and its absorbency is not linear. This means that a careful balance needs to be struck between absorbency, conformability and moisture vapour transmission.

There is a need for an absorbent component for use in wound dressings which is capable of absorbing exudate at the rate at which it is produced by the wound, which also does not cause maceration to the wound and skin surrounding the wound, which gives a reasonable wear time before needing to be replaced and which is conformable.

DETAILED DESCRIPTION OF THE INVENTION

We have now developed an absorbent component for a wound dressing which alleviates the above problems and there is provided by a first embodiment of the present invention an absorbent component for a wound dressing, the component comprising a wound contacting layer comprising gel forming fibres bound to a foam layer.

We have found that absorbent components according to the invention may mitigate the problems associated with the management of exudate. This is achieved by the combined use of a wound contact layer which absorbs exudate by gelling so that lateral spread of the exudate is contained, with a foam layer which absorbs exudate but readily releases it through moisture vapour transmission.

Surprisingly we have found that the absorbent wound contacting layer appears to control the fluid handling properties of the foam. We believe that the presence of the gel forming wound contact layer limits the lateral spread of exudate in the foam and increases its exudate retention compared to the use of foam alone. In turn the moisture vapour transmission properties of the wound contacting layer may be improved.

The wound contacting layer is present to transport wound fluid away from the wound and absorb it while containing the lateral spread of exudate. The absorbent component preferably has an absorbency of at least 10 g/g, preferably from 15 g/g to 50 g/g and most preferably an absorbency of from 20 g/g to 50 g/g. The wound contacting layer is fibrous and comprises gel-forming fibres. We have found that fibrous layers as opposed to polymeric layers have the advantage that they are especially able to gel block which resists the lateral spread of exudate. In addition exudate is absorbed rapidly and is retained under pressure.

The fibres suitable for use in the absorbent layer of the present invention include hydrophilic fibres, which upon the uptake of wound exudate become moist and slippery and gelatinous and thus reduce the tendency of the surrounding fibres to stick to the wound. The fibres can be of the type which retain their structural integrity on absorption of exudate or can be of the type which lose their fibrous form and become a structureless gel or a solution upon absorption of exudate.

The fibres are preferably chemically modified cellulose fibres and in particular spun sodium carboxymethylcellulose fibres or cellulose ethyl sulphonate fibres. The carboxymethylcellulose fibres are preferably as described in PCT W0/9312275 or GB93/01258. The fibres may also be pectin fibres, alginate fibres and particularly those as described in WO94/17227 or EP433354 or EP476756 or composite fibres of alginate and polysaccharide such as those described in EP 0892863, chitosan fibres, hyaluronic acid fibres, or other polysaccharide fibres or fibres derived from gums. The cellulosic fibres preferably have a degree of substitution of at least 0.05 carboxymethyl groups per cellulose unit.

Preferably the gel forming fibres for use in the present invention have an absorbency of either water or saline of at least 15 g/g as measured by the free swell absorbency method, more preferably at least 25 g/g or 50 g/g. The degree of substitution of the carboxymethylated cellulose gel forming fibres is preferably at least 0.2 carboxymethyl groups per cellulose unit, more particularly between 0.3 and 0.5.

The gel forming fibres are preferably mixed to give a wound contacting layer comprising fibres of different absorbencies or properties.

The wound contacting layer may comprise other fibres such as textile fibres which can be natural or synthetic, but are preferably cellulosic fibres for example viscose rayon, multi-limbed viscose, cotton or regenerated cellulose having a higher absorbency than most textile fibres. Textile fibres typically have an absorbency of less than 1 g/g when measured by the free swell absorbency test.

The wound contacting layer can be made from a non woven, fibrous web formed by any of the following methods: needle punched, spunlaced, wet-laid, dry laid, meltblown or felled. The web can then be stitch bonded with strengthening fibres or yarns to provide additional strength to the layer such that it retains its structure when saturated with exudate. Additionally the stitchbonded structure may afford higher absorbency or a degree of extensibility to the dressing depending on the nature of the strengthening fibres and yarns used and their stitchbonding pattern. The wound contacting layer is preferably between 20 microns and 5 mm thick, more preferably 2 mm to 3 mm thick and even more preferably from 1 mm to 2 mm thick.

The foam layer of the present invention is preferably a hydrophilic foam such as polyurethane and more preferably is a hydrophilic open celled foam such as those available from Polymer Health Technologies, Rynel or Filtrona and in particular Filtrona 30W. The foam typically has a thickness of 0.25 mm to 5 mm, preferably from 1 mm to 4.0 mm and most preferably from 1.5 mm to 3 mm. The foam layer preferably has an absorbency of 10 to 20 g/g when measured by the free swell absorbency method (BS EN 13726-1:2002)

The foam layer is bonded to the wound contacting layer preferably by a polymer based melt layer, by an adhesive, by flame lamination or by ultrasound. The foam layer may be directly bonded to the wound contact layer to make a laminate structure where the layers co-extend and are separated by the bonding line or the foam layer may form an island in the upper surface of the component surrounded by the wound contacting layer. By forming an island of foam in the upper surface of the absorbent component in this way, the tendency of the foam to laterally spread the exudate in the foam layer and rewet the wound contacting layer is physically limited.

A textile layer may be positioned between the wound contact layer and the foam layer to limit distortion of the component that may occur when the foam layer expands on absorption of exudate. The textile layer is preferably made from absorbent fibres such as polyester, nylon, or cotton which may contain superabsorbent components such as cross linked sodium polyacrylate or may be made from a superabsorbent fibre such as polyacrylate.

A one-way wicking layer may be positioned between the wound contact layer and the foam layer to assist in the prevention of exudate rewetting the wound contact layer outside the area of the wound by transfer down from the foam towards the wound. The one-way wicking layer has the property that it resists the passage of exudate in one direction. The one-way wicking layer may be Tredegar Premium embossed perforated film made from ethylene-methyl acrylate/Ethylene vinyl acetate.

A further aspect of the invention relates to a wound dressing comprising the absorbent component. In any wound dressing configuration, the absorbent component contacts the wound so that the gel-forming fibres absorb and retain wound exudate and control the lateral spread of exudate adjacent the wound. Preferably the absorbent component forms an island in direct contact with the wound surrounded by a periphery of adhesive that adheres the dressing to the wound. The adhesive holds the absorbent component in direct contact with the wound and may seal the dressing to the skin surrounding the wound.

The adhesive is preferably a silicone adhesive and more preferably a pressure sensitive silicone adhesive such as Dow Corning MD7-4502 or M67-9900. The adhesive may also be a hydrocolloid, polyurethane, rubber based adhesive or acrylic adhesive.

The dressing may also comprise a film layer forming the outer surface of the dressing. Preferably the film layer has an MVTR of at least 1500/m2/24 hrs. The film layer is present to provide a bacterial and viral barrier, control moisture vapour transmission and provide a low co-efficient of friction to the dressing.

The dressing may also comprise additional optional layers.

BRIEF DESCRIPTION OF THE DRAWINGS

Preferred embodiments of the invention will now be described by way of example with reference to the accompanying drawings in which:

Referring now to FIG. 1 of the drawings, the wound dressing comprises an absorbent component 2 comprising a wound contacting layer 4 bonded to a foam layer 6 by an adhesive 8. The component 2 is surrounded by an adhesive 10 so that the wound contacting layer 4 forms an island in the adhesive 10. The dressing has a thin film backing 12 bonded to the component 2 and adhesive 10 by an adhesive 14.

Similarly FIG. 2 shows a wound dressing comprising an absorbent component 2 comprising a wound contacting layer 4 bonded to a foam layer 6 with an adhesive. The component 2 is surrounded by adhesive 10, so that the wound contacting layer forms an island in the adhesive 10. The dressing has a thin film backing 12 bonded to the component 2 and adhesive 10 by an adhesive 14. The foam layer 6 of the component 2 is surrounded by the wound contacting layer 4 so that the foam is an island in the upper surface of the component 2. FIG. 2 shows the foam 6 surrounded by a periphery 16 of the wound contact layer 4.

FIG. 3 shows a wound dressing comprising an absorbent component 2 comprising a wound contacting layer 2 bonded to a one-way wicking layer 18 which surrounds a foam layer 6. The foam layer 6 forms an island in the one-way wicking layer 18 to assist in the prevention of the foam rewetting the wound contact layer. The surface of the absorbent component 2 furthest from the wound has an island of foam 6 surrounded by a periphery 20 of the one-way wicking layer. The component 2 is surrounded by an adhesive 10 so that the wound contacting layer 4 forms an island in the adhesive 10.

Example 1

Figure 1:
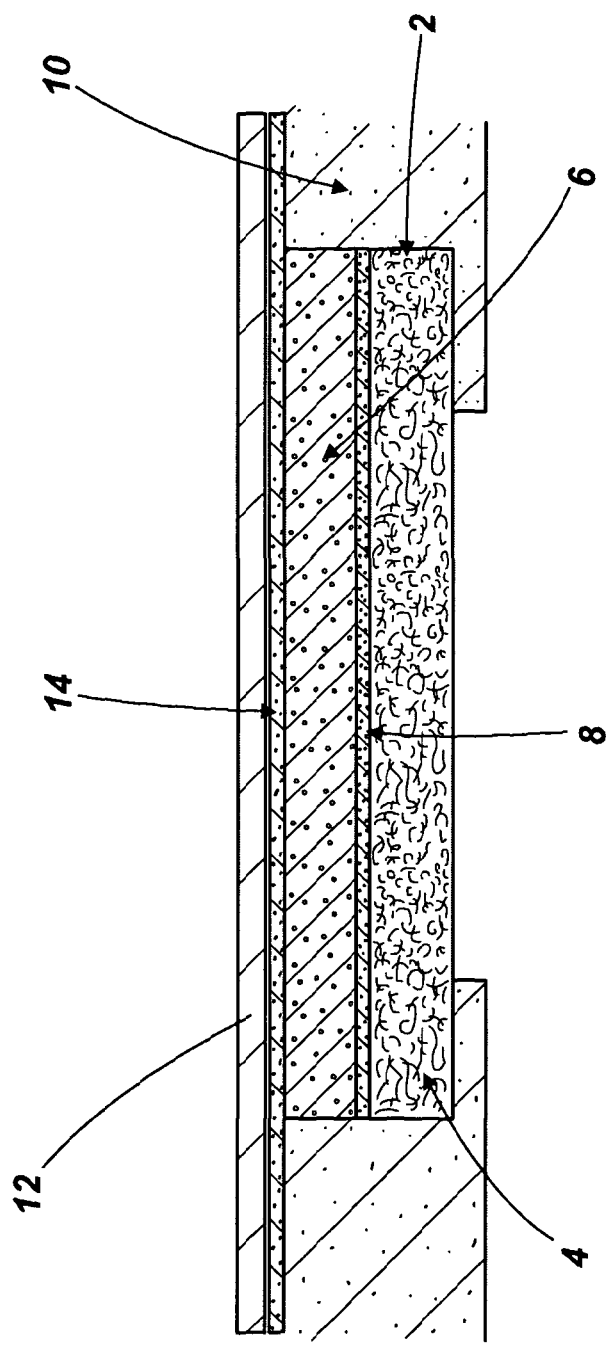
FIG. 1 is a cross sectional view of one embodiment of the wound dressing according to the invention.
Figure 2:
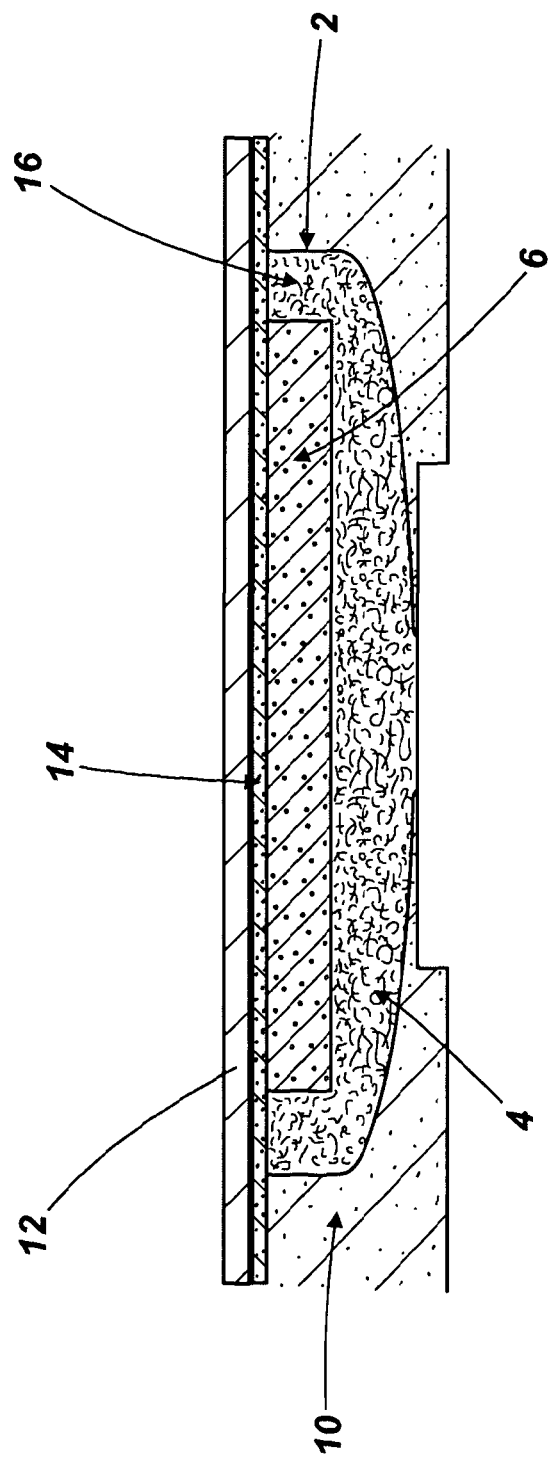
FIG. 2 is a cross sectional view of a further embodiment of the wound dressing according to the invention showing the foam as an island in the wound contacting layer.
Figure 3:
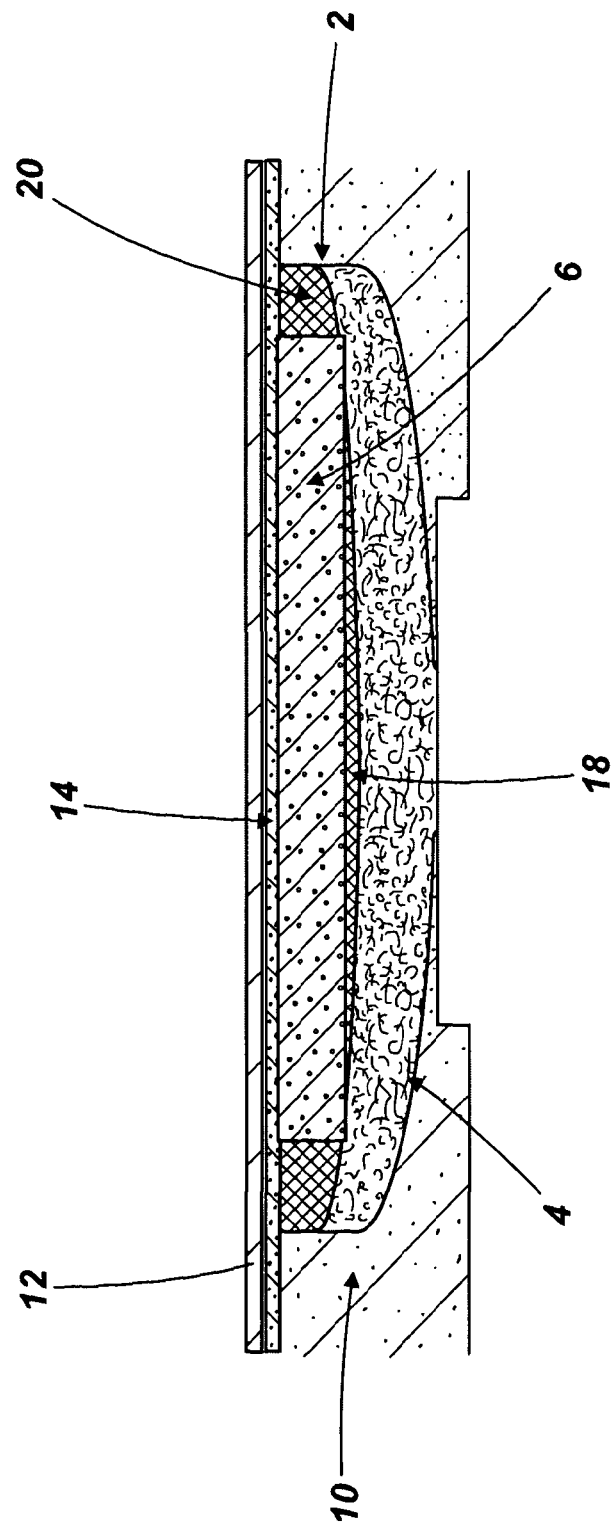
FIG. 3 is a cross sectional view of a further embodiment of the wound dressing according to the invention showing a one-way wicking layer separating the layers of the absorbent component.

The thickness, absorbency, retention and lateral spread of the various layers of the wound dressing component were measured alone and in combination.
Materials Used
20 gsm Vilmed (44262)
100 gsm Hydrofibere® Aquacel®™ ex ConvaTec
210 gsm Hydrofiber® Aquacele®™ ex ConvaTec
Polymer Health Technology (PHT) Foam (RM0056110)
Polymer Health Technology (PHT) Foam (RM0057/10)
Wound Dressing Component Four prototypes were constructed. Prototype construction began by bonding the relevant Hydrofiber® and foam together using one layer of 20 gsm Vilmed and the Prestex PFC 320 set at 200° C. and a motor speed of 1. The completed sheets were then cut to shape using a cutter and Wallace Cutting Press. The various combinations of materials are detailed below.

TABLE 1

Component details

| Foam | Hydrofiber ® |
|---|---|
| PHT 2.5 mm | 100 gsm Hydrofiber ® |
| PHT 5 mm | 100 gsm Hydrofiber ® |
| PHT 2.5 mm | 210 gsm Hydrofiber ® |
| PHT 5 mm | 210 gsm Hydrofiber ® |

Hydrofibre ® is a gel forming fibre sold in the product Aquacel ® ex ConvaTec.

Testing

Absorbency was measured as per BS EN 13726-1:2002 Test methods for primary wound dressings—Part 1: Aspects of Absorbency, Section 3.2.2 to 3.2.5. Following on from the absorbency test, the wet sample was removed from the balance and placed flat on to a perforated stainless steel plate and immediately covered by a weight equivalent to 40 mmHg (for a 5 cm×5 cm sample, weight 1358 g). The weight was left in place for 1 minute before being removed and the sample reweighed.

For determining the % Lateral Spread, the material to be tested was placed on a flat surface and a rigid tube with internal diameter of 29 mm was placed on the centre and held in place. 20 mls of horse serum was injected into the tube and left for 60 seconds. After 60 seconds had elapsed, any non-absorbed fluid was removed from the material surface with a syringe before removing the vial. A ruler was placed below the dressing and a photograph taken with a digital camera. The area of lateral fluid spread was measured by analyses of photograph in an Image Analyses software package. The percentage lateral spread was calculated as follows:

[(Lateral spread area/vial area)×100]−100

Results

TABLE 2

Fluid absorbed/retained by dressing

| Sample Details | Fluid Absorbed per unit area(g/cm2) | Percentage Retained (%) |
|---|---|---|
| Vilmed | 0.011 | 43.87 |
| 100 gsm Hydrofiber | 0.167 | 80.04 |
| 210 gsm Hydrofiber | 0.274 | 91.50 |
| 2.5 mm PHT Foam | 0.479 | 63.19 |
| 5 mm PHT Foam | 0.779 | 68.88 |

TABLE 2-continued

Fluid absorbed/retained by dressing

| Sample Details | Fluid Absorbed per unit area(g/cm2) | Percentage Retained (%) |
|---|---|---|
| 100 gsm Hydrofiber☐ Laminated to 2.5 mm PHT Foam | 0.507 | 77.63 |
| 100 gsm Hydrofiber☐ Laminated to 5 mm PHT Foam | 0.517 | 80.86 |
| 210 gsm Hydrofiber☐ Laminated to 2.5 mm PHT Foam | 0.747 | 74.81 |
| 210 gsm Hydrofiber☐ Laminated to 5 mm PHT Foam | 0.780 | 77.12 |

Results quoted are the mean of n=3

It can be seen from the results that doubling the weight of the Hydrofiber or the thickness of foam does not increase the fluid absorbing properties of the materials by a factor of 2. Therefore increasing the thickness of either of these materials does not provide an optimum solution to increasing the absorbency of the dressing as conformability is compromised. Combining the technologies gives a synergy between absorbency and retention. It can also be seen that the PHT foams' ability to retain fluid is less than that of Hydrofiber.

TABLE 3

Lateral Spread

| Sample Details | Lateral Spread % | Lateral Spread after 60 seconds under 40 mmHg pressure |
|---|---|---|
| 100 gsm Hydrofiber | 12.20 | 216.69 |
| 210 gsm Hydrofiber | 22.27 | 51.67 |
| 2.5 mm PHT Foam | 64.99 | 748.58 |
| 5 mm PHT Foam | 88.40 | 420.49 |
| 100 gsm Hydrofiber☐ Laminated to 2.5 mm PHT Foam | 28.56 | 205.04 |
| 100 gsm Hydrofiber☐ Laminated to 5 mm PHT Foam | 30.03 | 147.29 |
| 210 gsm Hydrofiber☐ Laminated to 2.5 mm PHT Foam | 15.59 | 41.18 |
| 210 gsm Hydrofiber☐ Laminated to 5 mm PHT Foam | 29.18 | 45.13 |

Results quoted axe the mean of n=3.

These results show that the wound contact layer controls lateral spread to a greater degree than does foam. Combining the wound contact layer and foam significantly reduces lateral wicking compared to foam alone.

What is claimed:

1. An absorbent component for a wound dressing, the component comprising a wound contacting layer comprising gel forming fibres consisting essentially of carboxymethylcellulose fibres, cellulose ethyl sulphonate, pectin fibres, alginate fibres, composite fibres of alginate and polysaccharide, chitosan fibres, polysaccharide fibres, fibres derived from gums or a mixture thereof, bound to a foam layer comprising an absorbency of 10-20 g/g when measured by the free swell absorbency method, wherein the foam layer is bound directly to the wound contacting layer by adhesive, polymer based melt layer, flame lamination or ultrasound, wherein the wound contacting layer is configured to absorb exudate by gelling and provides containment of lateral spread of the exudate and the foam layer is configured to absorb exudate but readily releases it through moisture vapour transmission.

2. The absorbent component for a wound dressing as claimed in claim 1, wherein the absorbent component is in sheet form.

3. The absorbent component for a wound dressing as claimed in claim 1, wherein the gel forming fibres are woven, non-woven and/or knitted.

4. The absorbent component for a wound dressing as claimed in claim 1, wherein the foam layer is an open cell foam.

5. The absorbent component for a wound dressing as claimed in claim 1, wherein the foam layer is a hydrophilic foam.

6. The absorbent component for a wound dressing as claimed in claim 1, wherein the foam layer comprises a thickness of 0.25 mm to 5 mm.

7. An absorbent component for a wound dressing, the component comprising a wound contacting layer comprising gel forming fibres consisting essentially of carboxymethylcellulose fibres, cellulose ethyl sulphonate, pectin fibres, alginate fibres, composite fibres of alginate and polysaccharide, chitosan fibres, polysaccharide fibres, fibres derived from gums or a mixture thereof, bound to a foam layer comprising a thickness of 0.25 mm to 5 mm, wherein the foam layer is bound directly to the wound contacting layer by adhesive, polymer based melt layer, flame lamination or ultrasound, wherein the wound contacting layer is configured to absorb exudate by gelling and provide containment of lateral spread of the exudate and the foam layer is configured to absorb exudate but readily releases it through moisture vapour transmission.

8. The absorbent component for a wound dressing as claimed in claim 7, wherein the absorbent component is in sheet form.

9. The absorbent component for a wound dressing as claimed in claim 7, wherein the gel forming fibres are woven, non-woven and/or knitted.

10. The absorbent component for a wound dressing as claimed in claim 7, wherein the foam layer is an open cell foam.

11. The absorbent component for a wound dressing as claimed in claim 7, wherein the foam layer is a hydrophilic foam.

12. A wound dressing comprising an absorbent component having a wound contacting layer with gel forming fibres consisting essentially of carboxymethylcellulose fibres, cellulose ethyl sulphonate, pectin fibres, alginate fibres, composite fibres of alginate and polysaccharide, chitosan fibres, polysaccharide fibres, fibres derived from gums or a mixture thereof, bound to a foam layer comprising a thickness of 0.25 mm to 5 mm, wherein the foam layer is bound directly to the wound contacting layer by a first adhesive, polymer based melt layer, flame lamination or ultrasound, wherein the wound contacting layer is configured to absorb exudate by gelling and provide containment of lateral spread of the exudate and the foam layer is configured to absorb exudate but readily releases it through moisture vapour transmission; and a second adhesive for holding the absorbent component in contact with the wound.

13. The wound dressing as claimed in claim 12, wherein the absorbent component is capable of forming an island in direct contact with the wound surrounded by a periphery of the second adhesive.

14. The wound dressing as claimed in claim 12, wherein the second adhesive is a silicone adhesive.

15. The wound dressing as claimed in claim 12, wherein the dressing is covered by a film layer on a surface of the dressing furthest from the wound.

\* \* \* \* \*